(12) United States Patent
Lee et al.

(10) Patent No.: US 9,192,791 B2
(45) Date of Patent: *Nov. 24, 2015

(54) TOPICAL COMPOSITION CONTAINING THEANINE DERIVATIVES FOR USE ON SKIN

(71) Applicant: AMOREPACIFIC CORPORATION, Seoul (KR)

(72) Inventors: Jin Young Lee, Yongin-si (KR); Jae Won Yoo, Yongin-si (KR); Hyang Tae Choi, Yongin-si (KR); Han Byul Kim, Yongin-si (KR); Sung Hoon Lee, Yongin-si (KR); Ji Seong Kim, Yongin-si (KR); Ji Hyun Bae, Yongin-si (KR)

(73) Assignee: Amorepacific Corporation, Seoul (KR)

( * ) Notice: Subject to any disclaimer, the term of this patent is extended or adjusted under 35 U.S.C. 154(b) by 0 days.

This patent is subject to a terminal disclaimer.

(21) Appl. No.: 14/360,371

(22) PCT Filed: Nov. 8, 2012

(86) PCT No.: PCT/KR2012/009377
§ 371 (c)(1),
(2) Date: May 23, 2014

(87) PCT Pub. No.: WO2013/077574
PCT Pub. Date: May 30, 2013

(65) Prior Publication Data
US 2014/0357593 A1    Dec. 4, 2014

(30) Foreign Application Priority Data

Nov. 23, 2011 (KR) .................. 10-2011-0122748
Nov. 7, 2012 (KR) .................. 10-2012-0125391

(51) Int. Cl.
| | |
|---|---|
| *A61K 31/7016* | (2006.01) |
| *A61Q 19/00* | (2006.01) |
| *A61Q 19/08* | (2006.01) |
| *A61K 9/00* | (2006.01) |
| *A61K 8/49* | (2006.01) |

(52) U.S. Cl.
CPC ............. *A61Q 19/007* (2013.01); *A61K 8/498* (2013.01); *A61K 9/0014* (2013.01); *A61K 31/7016* (2013.01); *A61Q 19/08* (2013.01)

(58) Field of Classification Search
None
See application file for complete search history.

(56) References Cited

U.S. PATENT DOCUMENTS 8,557,793 B2 * 10/2013 Yoo et al. ............... 514/53
2008/0009505 A1 * 1/2008 Hodges et al. ........ 514/255.01

FOREIGN PATENT DOCUMENTS

| KR | 10-0513616 B1 | 9/2005 |
| KR | 10-2009-0064743 A | 6/2009 |

* cited by examiner

*Primary Examiner* — Traviss C McIntosh, III
(74) *Attorney, Agent, or Firm* — Sughrue Mion, PLLC

(57) ABSTRACT

The present invention relates to a topical composition for use on skin containing theanine derivatives as active components and, more particularly, to a topical composition for use on skin having anti-aging, skin wrinkle repair, skin barrier enhancement, skin immunity enhancement, skin moisturizing, and atopy alleviation effects by containing theanine derivatives as active components.

15 Claims, 3 Drawing Sheets

TOPICAL COMPOSITION CONTAINING THEANINE DERIVATIVES FOR USE ON SKIN

CROSS REFERENCE TO RELATED APPLICATIONS

This application is a National Stage of International Application No. PCT/KR2012/009377 filed Nov. 8, 2012, claiming priority based on Korean Patent Applications Nos. 10-2011-0122748 filed Nov. 23, 2011 and 10-2012-0125391 filed Nov. 7, 2012, the contents of all of which are incorporated herein by reference in their entirety.

TECHNICAL FIELD

The present invention relates to a skin preparation composition for external use containing a theanine derivative as an active ingredient and, more particularly to, a skin preparation composition for external use that contains a theanine derivative as an active ingredient to have an anti-aging effect, improve skin wrinkles, strengthen skin barriers and skin immunity, and improve skin moisturization and atopic skin troubles.

BACKGROUND ART

Theanine is an amino acid primarily found in green tea (Camellia sinesis) and produced by an enzyme reaction of L-glutamine and ethylamine. Generally, theanine takes about 1 to 2 wt. % with respect to the total dry weight of green tea leaves and exists primarily in the form of free amino acid. It is reported that theanine suppresses the stimulant action of caffeine (Toxicol Lett. 2001 123(2-3), 159-167, Biosci. Biotechnol. Biochem. 2000 February; 64(2):287-93), increases alpha-waves in the brain to alleviate the stress (Nippon Nogeikagaku Kaishi 1998; 72:153-157) and has an anti-stress effect, such as inhibiting the increase in the cardiac impulses caused by the stress and reducing the factors on the stress reaction (Bio Psychol. 2007 74(1):39-45). Theanine is also reported to have a cancer-fighting action by reducing the level of glutathione in the cancer cells (Cancer Lett. 2004 212(2), 177-184), drop the blood pressure (Biosci Biotechnol Biochem 1995 59(4) 615-618) and partly exert an antioxidant function of inhibiting the oxidization of low-density lipoprotein cholesterol (LDL-cholesterol) (Exp Toxicol Pathol 1997; 49:329-335). Recently, some studies have been made on the physiological activities of theanine, such as having an anti-obesity function (In Vivo 2004, 18(1) 55-62) and increasing levels of enzymes participating in alcoholysis.

The probability that theanine has various physiological activities has been investigated and specifically studied. But, what it comes to the dermatological region, there have never been reported any known studies or reports on the dermatological efficacies of theanine and their related mechanisms, except for the activities of theanine and catechin, an ingredient of green tea, when used alone or in combination, such as breaking down fat (Korean Laid-open Patent Publication No. 2004-0092538), improving skin aging (Korean Laid-open Patent Publication No. 2007-0028901) and promoting pro-line recycling (Korean Laid-open Patent Publication No. 2009-0064743). US2006/0134095 A1 discloses the moisturizing effect of theanine and the theanine derivative as a cell activator. But, not much is known about the excellent dermatological efficacies of theanine derivatives other than theanine.

DISCLOSURE OF INVENTION

Accordingly, the inventors of the present invention have found out the fact that the theanine derivative benefits from its characteristic physiological activities to have more excellent and differentiated physiological efficacies, more than imitating the effects of the theanine mother nuclei, such as providing an anti-aging effect, improving skin wrinkles, strengthening skin barriers and skin immunity, and improving skin moisturization and atopic skin troubles, thereby completing the present invention.

It is therefore an object of the present invention to provide a skin preparation composition for external use that contains a theanine derivative as an active ingredient and thus provide excellent efficacies to have an anti-aging effect, improve skin wrinkles, strengthen skin barriers and skin immunity, and improve skin moisturization and atopic skin troubles.

The present invention is directed to a skin preparation composition for external use that contains a theanine derivative as an active ingredient to have an anti-aging effect, improve skin wrinkles, strengthen skin barriers and skin immunity, and improve skin moisturization and atopic skin troubles.

The skin preparation composition for external use containing a theanine derivative according to the present invention can benefit from the physiological activities of the theanine derivative to have more excellent and differentiated physiological efficacies, more than imitating the effects of the theanine mother nuclei, such as providing an anti-aging effect, improving skin wrinkles, strengthening skin barriers and skin immunity, and improving skin moisturization and atopic skin troubles.

BEST MODES FOR CARRYING OUT THE INVENTION

Figure 1:
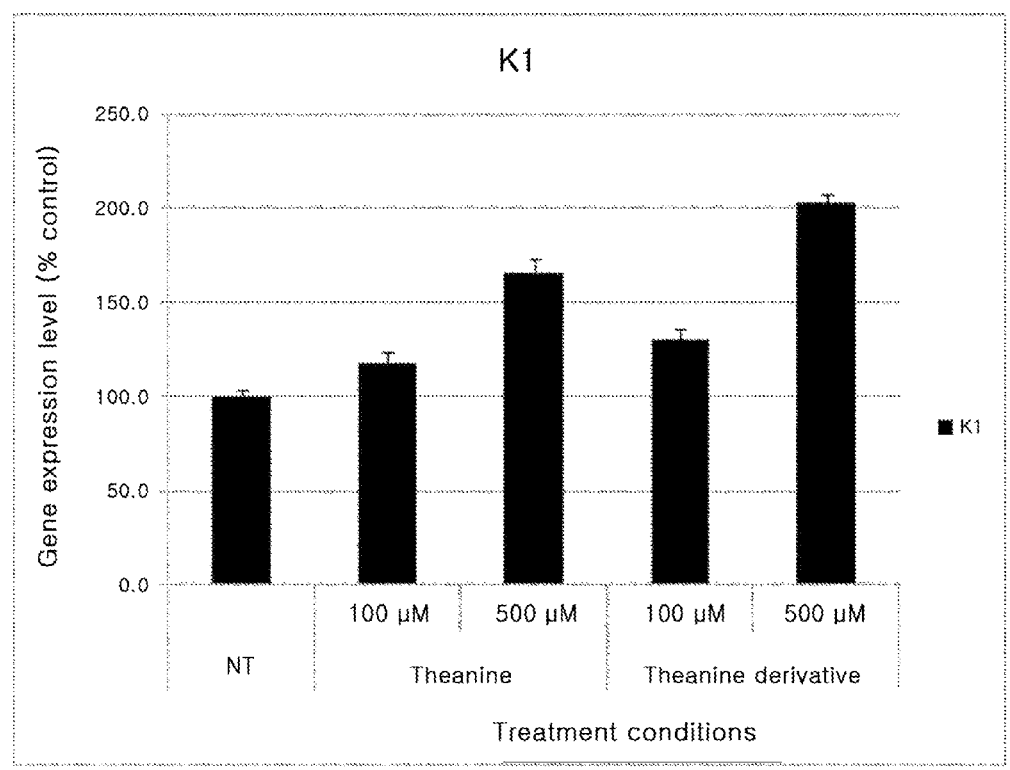
FIG. 1 is a graph showing a comparison of Keratin 1 gene expression by theanine and the theanine derivative of the present invention.

Hereinafter, the present invention will be described more specifically.

The theanine derivative used in the present invention has a structure of the following formula 1 or 2:

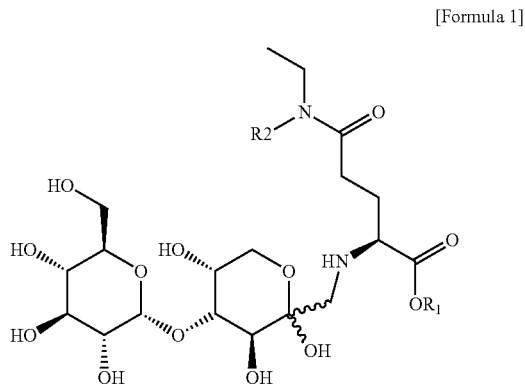

[Formula 1]

(In this formula, $R_1$ is selected from the group consisting of hydrogen, methyl, ethyl, propyl, isopropyl, n-butyl, isobutyl, and tert-butyl; and $R_2$ is selected from the group consisting of hydrogen, methyl, ethyl, propyl, isopropyl, n-butyl, isobutyl, and tert-butyl)

[Formula 2]

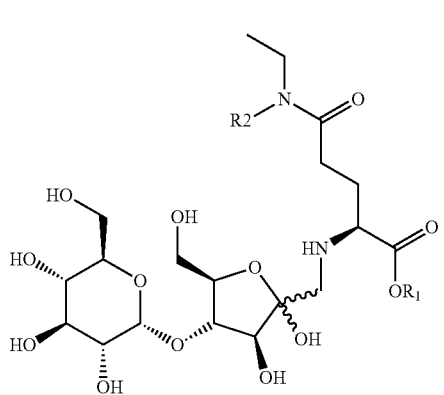

(In this formula, $R_1$ is selected from the group consisting of hydrogen, methyl, ethyl, propyl, isopropyl, n-butyl, isobutyl, and tert-butyl; and $R_2$ is selected from the group consisting of hydrogen, methyl, ethyl, propyl, isopropyl, n-butyl, isobutyl, and tert-butyl)

Preferably, the content of the theanine derivative of the present invention is 0.0001 to 20 wt. % with respect to the total weight of the composition. The content of the theanine derivative less than 0.0001 wt. % leads to failure to provide a desired effect, whereas the content of the theanine derivative greater than 20 wt. % makes it hard to control the viscosity of the cosmetic formulation.

The skin epidermis completely develops keratin through cell proliferation and differentiation and becomes worn away continuously. This process is called "epidermal homeostasis". During this process, the keratinocytes divided in the basal layer synthesize various proteins and lipids and become keratin cells to form a cornified layer. As the basal cells in the epidermis differentiate, cell nuclei and other organelles within the cells disappear to flatten the basal cells and increase keratin intermediate filaments. In the cell differentiation, the intercellular calcium concentration is of importance. The keratinocytes undergo proliferation accelerated in the bottom part of the epidermis where the intercellular calcium concentration is low, while they differentiate rather than proliferate in the top of the epidermis where the intercellular calcium concentration is high. The keratin protein constituting the keratin intermediate filaments expresses keratin 5 and Keratin 14 in the basal layer and Keratin 1 and Keratin 10 in the granular layer. Therefore, Keratin 1 is used as an indicator of epidermal differentiation.

Skin aging is classified into photoaging and chronological aging. In both cases, the aged skin has different features in the epidermis from the young skin. The photoaging features an abnormal increase in the thickness of the epidermis, and the chronological aging reduces the thickness of the epidermis and keeps the keratin cells not shedding off. Both of these cases result from the failure to have normal turn-over process of the epidermis and inappropriate control of epidermal differentiation. Further, such changes of the epidermis are related to the occurrence of wrinkles in the photoaging, as described in a paper (JDS, 2001 Kambaytashi) in which hairless mice are subjected to an exposure to chronic low-level UV irradiation to study the mechanism of wrinkling. According to the paper, the skin exposed to UV irradiation is susceptible to wrinkling, with a remarkable drop of the levels of Keratin 1 and filaggrin.

The theanine derivative of the present invention has an effect to increase the expression of Keratin 1 and thus improve epidermal homeostasis balancing proliferation and differentiation in the epidermis. This can improve chronological skin aging and prevent or alleviate UV-induced wrinkling.

One of the most important functions of the skin is to form a barrier preventing migration of various substances through the skin. As for the skin barrier, keratin intermediate filaments when abruptly moving from the granulate layer to the cornified layer agglomerate to form filament bundles, which become crosslinked with the protein components and another cytoplasmic proteins existing in the keratin free granules to form a keratin protein layer surrounding the inner side of the cell membrane and substitute for the cell membrane. The keratin protein layer combines with the keratin lipid membrane to form a cornified envelope constituting a boundary between keratinocytes, completing a perfect skin barrier structure. Filaggrin serves to accelerate the association of keratin filaments in the cornified layer and the granulate layer and strengthen the barrier. Transglutaminase 1 cross-links various proteins required to form the cornified envelope and combines the long-chain hydroxyceramide with the proteins, contributing to the formation of the keratin lipid membrane.

The theanine derivative of the present invention is excellent in promoting the expression of filaggrin and transglutaminase 1. Therefore, the theanine derivative of the present invention has an effect of helping the formation of the cornified envelope to strengthen the primary function of the skin, the skin barrier function. This can make the physical barrier of the skin stronger to enhance the innate immunity of the skin.

The natural moisturizing factor (NMF), one of the important factors in moisturizing the skin, consists of amino acids and their derivatives, contains water and maintains moisture in the skin. Its efficacy of strengthening the skin barrier is also a factor that contributes to the skin moisturizing effect. Also, filaggrin decomposes into amino acids to form a natural moisturizing factor, apart from its effect to accelerate the association of keratin filaments in the cornified layer and the granulate layer and strengthen the skin barrier. Further, periodical reports have been made to implicit that the abnormal filaggrin gene is related to the symptoms as a prelude to atopic dermatitis. Accordingly, filaggrin strengthens the skin barrier function of the epidermis, serves as a natural moisturizing factor, and has a close relation to atopic dermatitis.

As already described above, the theanine derivative of the present invention increases the expression of filaggrin. This can strengthen the skin barrier function of the epidermis, increase the natural moisturizing factors to provide a skin moisturizing effect and alleviate the symptoms of atopic dermatitis caused by the reduction of filaggrin.

The formulation of the cosmetic composition is not specifically limited and may be appropriately selected depending on the use purpose of the cosmetic composition. For example, the cosmetic composition may be formulated into at least one selected from the group consisting of, if not limited to, emulsion, skin softener, skin toner, astringent, lotion, milk lotion, moisturizing lotion, nutrient lotion, massage cream, nutrient cream, moisture cream, hand cream, makeup foundation, essence, nutrient essence, face mask, soap, foaming cleanser, lotion type cleanser, cream type cleanser, body lotion, and body cleanser.

When the formulation of the present invention is a paste, cream, or gel, the suitable carrier may be animal fibers, plant fibers, wax, paraffin, starch, tragacanth gum, cellulose derivatives, polyethylene glycol, silicone bentonite, silica, talc, zinc oxide, etc.

When the formulation of the present invention is a powder or a spray, the suitable carrier may be lactose, talc, silica, aluminum hydroxide, calcium silicate, or polyamide powder. Particularly, the spray formulation may additionally include a propellant, such as chlorofluorohydrocarbon, propane/butane, or dimethyl ether.

When the formulation of the present invention is a solution or an emulsion, the suitable carrier may be a solvent, a solubilizing agent, or an emulsifying agent, such as, for example, water, ethanol, isopropanol, ethyl carbonate, ethyl acetate, benzyl alcohol, benzyl benzoate, propylene glycol, 1,3-butylglycol oil, glycerol aliphatic ester, polyethylene glycol, or fatty acid ester of sorbitan.

When the formulation of the present invention is a suspension, the suitable carrier may be a liquid diluent (e.g., water, ethanol, or propylene glycol), a suspension (e.g., ethoxylated isostearyl alcohol, polyoxyethylene sorbitol ester, or polyoxyethylene sorbitan ester), microcrystalline cellulose, aluminum methahydroxide, bentonite, agar, or tragacanth gum.

When the formulation of the present invention is a surfactant-containing cleanser, the suitable carrier may be aliphatic alcohol sulfate, aliphatic alcohol ether sulfate, sulfosuccinic acid monoester, isethionate, imidazolinium derivative, methyltaurate, sarcosinate, fatty acid ether sulfate, alkylamidobetaine, aliphatic alcohol, fatty acid glyceride, fatty acid diethanolamide, vegetable oil, lanolin derivative, or ethoxylated glycerol fatty acid ester.

The cosmetic composition may further include functional additives and ingredients included in general cosmetic compositions in addition to the theanine derivative. For example the functional additives may include a component selected from the group consisting of water-soluble vitamins, oil-soluble vitamins, polymer peptide, polymer polysaccharides, sphingolipids, and seaweed extract.

Under necessity, the cosmetic composition of the present invention may further include ingredients of general cosmetic compositions in combination with the aforementioned functional additives. Those ingredients may include oils, moisturizing agents, emollients, surfactants, organic/inorganic pigments, organic powder, UV absorbers, preservatives, antibacterial agents, antioxidants, vegetable extracts, pH regulators, alcohols, colorants, fragrances, blood circulation accelerators, cold active agents, antifreezing agents, purified water, etc.

MODES FOR CARRYING OUT THE INVENTION

Hereinafter, the present invention will be described further specifically with reference to the following examples and experimental examples, which are not intended to limit the scope of the present invention.

Experimental Example 1

Examination of Expression of Keratin 1 Gene in Human Neonatal Epidermal Keratinocytes (HEK)

Human neonatal epidermal keratinocytes (HEK, Lonza, NHEK-Neo-Neonatal Normal Human Epidermal Keratinocytes, Pooled) are dispensed in medium (KBM-gold, Lonza) in a 6-well plate at a density of $1 \times 10^5$ cells per well and cultured at 37° C. for 24 hours, after which the medium is eliminated. Then, the theanine derivative is treated with media (KBM-gold, Lonza) each containing 100 μM or 500 μM, which are used to incubate HEK cells at 37° C. for 5 days.

Then, RNA is extracted from the HEK cells incubated for 5 days using an RNeasy mini kit (Qiagen), and a cDNA is synthesized through an RT-PCR process using a Superscript III kit (Invitrogen). To examine the expression level of Keratin 1, a probe (TaqMan™ fluorogenic probe, Hs00196158_m1) is used to conduct the quantitative real-time PCR process and observe the expression behavior of Keratin 1. The results are presented in FIG. 1. The control is the non-treated group, treated with 100 μM or 500 μM theanine (Sigma, T6576) other than the theanine derivative.

As can be seen from FIG. 1, the theanine derivative has an effect to increase the expression of Keratin 1, as compared with the non-treated group. Further, the theanine derivative has a considerably stronger effect in comparison with the mother nucleus of theanine at the same concentration.

Experimental Example 2

Examination of Expression of Transglutaminase 1 Gene in Human Neonatal Epidermal Keratinocytes (HEK)

Human neonatal epidermal keratinocytes (HEK, Lonza, NHEK-Neo-Neonatal Normal Human Epidermal Keratinocytes, Pooled) are dispensed in medium (KBM-gold, Lonza) in a 6-well plate at a density of $1 \times 10^5$ cells per well and cultured at 37° C. for 24 hours, after which the medium is eliminated. Then, the theanine derivative is treated with media (KBM-gold, Lonza) each containing 100 μM or 500 μM, which are used to incubate HEK cells at 37° C. for 5 days.

Then, RNA is extracted from the HEK cells incubated for 5 days using an RNeasy mini kit (Qiagen), and a cDNA is synthesized through an RT-PCR process using a Superscript III kit (Invitrogen). To examine the expression level of transglutaminase 1, a probe (TaqMan™ fluorogenic probe, Hs00165929_m1) is used to conduct the quantitative real-time PCR process and observe the expression behavior of transglutaminase 1. The results are presented in FIG. 2. The control is the non-treated group, treated with 100 μM or 500 μM theanine (Sigma, T6576) other than the theanine derivative.

Figure 2:
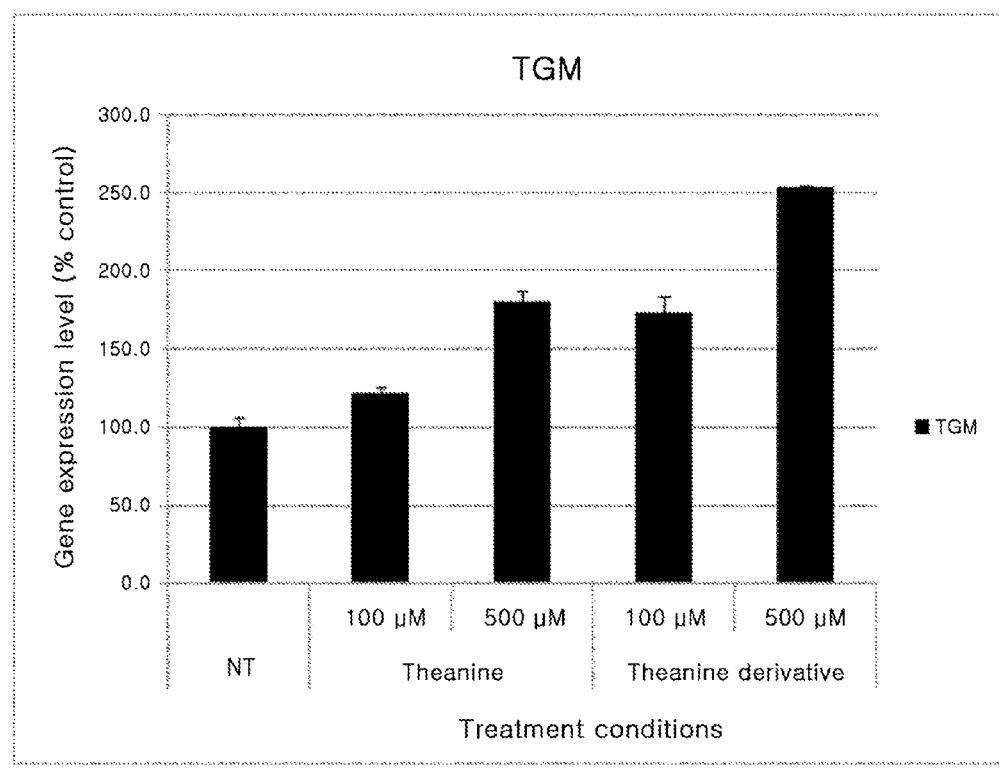
FIG. 2 is a graph showing a comparison of transglutaminase 1 gene expression by theanine and the theanine derivative of the present invention.

As can be seen from FIG. 2, the theanine derivative has an effect to increase the expression of transglutaminase 1, as compared with the non-treated group. Further, the theanine derivative has a considerably stronger effect in comparison with the mother nucleus of theanine at the same concentration.

Experimental Example 3

Examination of Expression of Filaggrin Gene in Human Neonatal Epidermal Keratinocytes (HEK)

Human neonatal epidermal keratinocytes (HEK, Lonza, NHEK-Neo-Neonatal Normal Human Epidermal Keratinocytes, Pooled) are dispensed in medium (KBM-gold, Lonza) in a 6-well plate at a density of $1 \times 10^5$ cells per well and cultured at 37° C. for 24 hours, after which the medium is eliminated. Then, the theanine derivative is treated with media (KBM-gold, Lonza) each containing 100 μM or 500 μM, which are used to incubate HEK cells at 37° C. for 5 days.

Then, RNA is extracted from the HEK cells incubated for 5 days using an RNeasy mini kit (Qiagen), and a cDNA is synthesized through an RT-PCR process using a Superscript III kit (Invitrogen). To examine the expression level of filaggrin, a probe (TaqMan™ fluorogenic probe, Hs00856927_m1) is used to conduct the quantitative realtime PCR process and observe the expression behavior of filaggrin. The results are presented in FIG. 3. The control is the non-treated group, treated with 100 μM or 500 μM theanine (Sigma, T6576) other than the theanine derivative.

Figure 3:
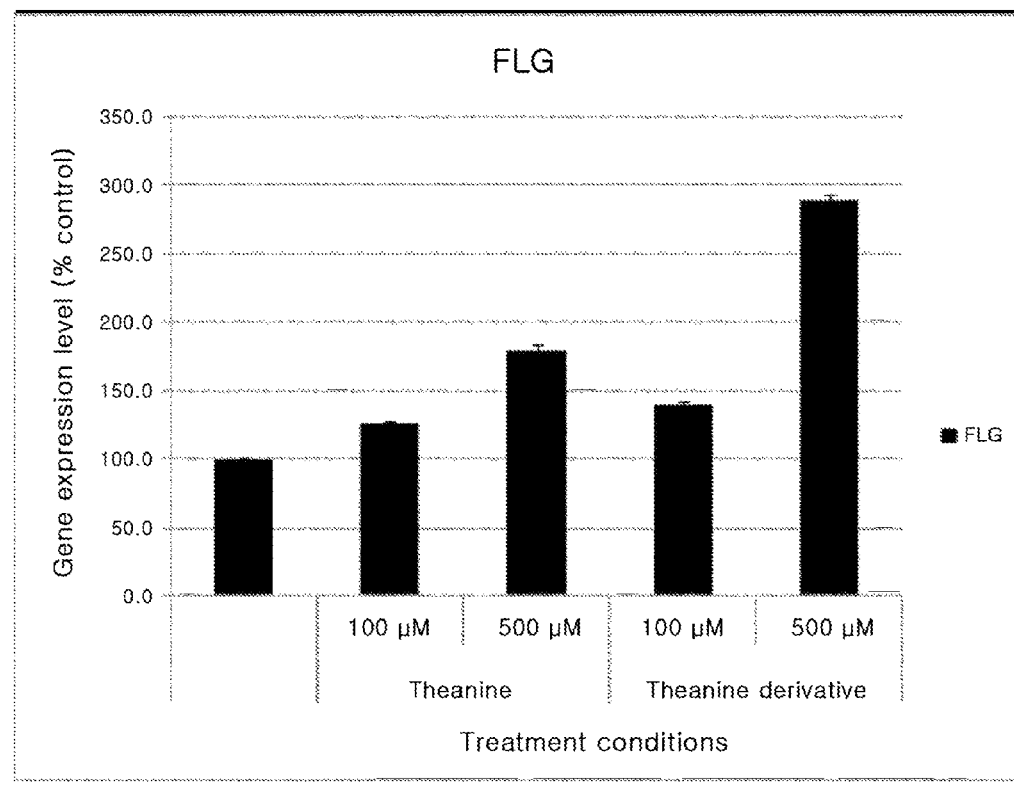
FIG. 3 is a graph showing a comparison of filaggrin gene expression by theanine and the theanine derivative of the present invention.

As can be seen from FIG. 3, the theanine derivative has an effect to increase the expression of filaggrin, as compared with the non-treated group. Further, the theanine derivative has a considerably stronger effect in comparison with the mother nucleus of theanine at the same concentration.

Experimental Example 4

Evaluation of Calcium Influx in Human Neonatal Epidermal Keratinocytes (HEK)

Stabilized human neonatal epidermal keratinocytes (HEK, Lonza, NHEK-Neo-Neonatal Normal Human Epidermal Keratinocytes, Pooled) are dispensed in a confocal dish at a density of $2\times10^4$ cells per well and treated with theanine (2.5 mM) and the theanine derivative (0.5 mM) for 5 minutes and then with 1 μm fluo 3-AM for 15 minutes. The fluo 3 decomposed in the cells and combined with calcium is observed with a confocal microscope (Nikon, Japan) to measure the difference of fluorescence and evaluate the migration of calcium in the cells. The results are presented in FIG. 4.

Figure 4:
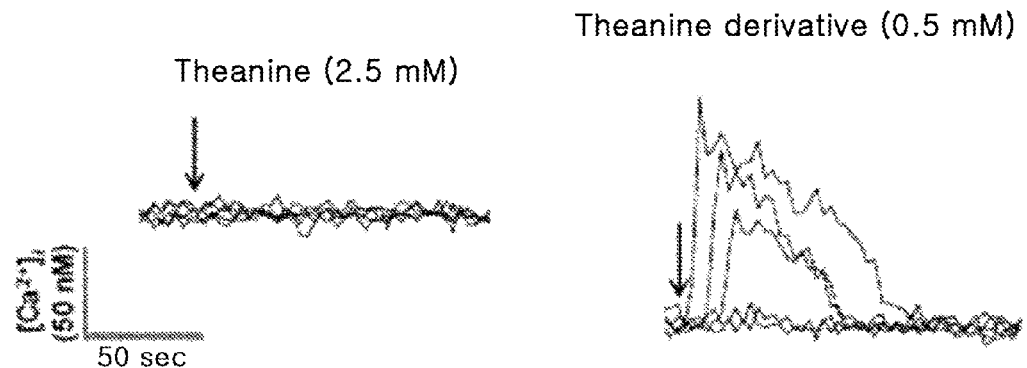
FIG. 4 shows the migration behavior of calcium in cells treated with theanine or the theanine derivative of the present invention.

As can be seen from FIG. 4, theanine and the theanine derivative show definitely different behaviors from each other in regards to the migration of calcium in the cells. This difference demonstrates that the theanine derivative of the present invention does not just imitate the effects of the mother nuclei of theanine but provides new physiological activities totally differentiated from the effects of the mother nuclei of theanine.

Example 1 and Comparative Example 1

Example 1 and Comparative Example 1 are prepared according to the following compositions given by Table 1.

TABLE 1

| Ingredient (Unit: wt. %) | Example 1 | Comparative Example 1 |
|---|---|---|
| Purified water | 69 | 70 |
| Propylene glycol | 30 | 30 |
| Theanine derivative | 1 | — |

Experimental Example 5

Measurement of Effect for Recovering Skin Barrier Function

The following experimental procedures are carried out to measure the effect of the theanine derivative to recover the skin barrier function in the damaged skin. For ten male or female adults, the skin barrier on the upper arm is damaged by the tape stripping method. Comparative Example 1 and Example 1 are applied to the damaged region in area of 3 cm×3 cm daily (once a day) in an amount of 2 mg/cm², and the recovery rate of the transepidermal water loss (TWEL) is measured with a Vapometer (Delfin, Finland) daily for 7 days. The transepidermal water loss is calculated, under the condition that the transepidermal water content before the tape stripping procedure is 100%. The results are presented in Table 2.

TABLE 2

| | TWEL change (%) | | | | | | |
|---|---|---|---|---|---|---|---|
| Test group | Before treatment | 1 day | 2 day | 3 day | 4 day | 5 day | 6 day |
| Example 1 | 100 | 86 | 73 | 54 | 31 | 31 | 31 |
| Comparative Example 1 | 100 | 120 | 113 | 97 | 70 | 61 | 43 |

As can be seen from Table 2, the use of Example 1 containing the theanine derivative turns the transepidermal water loss to normal apace and recovers the skin barrier.

Example 2 and Comparative Example 2

The compositions given by the following Table 3 are adopted to formulate the nutrient creams of Example 2 and Comparative Example 2.

TABLE 3

| Ingredient (wt. %) | Example 2 | Comparative Example 2 |
|---|---|---|
| Purified water | To 100 | To 100 |
| Theanine derivative | 1 | — |
| Hydrogenated vegetable oil | 1.50 | 1.50 |
| Stearic acid | 0.60 | 0.60 |
| Glycerol stearate | 1.00 | 1.00 |
| Stearyl alcohol | 2.00 | 2.00 |
| Polyglyceryl-10 pentastearate & Behenyl alcohol & sodium stearoyl lactylate | 1.00 | 1.00 |
| Arachidyl Behenyl alcohol & arachidyl glucoside | 1.00 | 1.00 |
| Cetylaryl alcohol & cetearyl glucoside | 2.00 | 2.00 |
| PEG-100 stearate & glyceroloeate & propylene glycol | 1.50 | 1.50 |
| Caprylic/capric triglyceride | 11.00 | 11.00 |
| Cyclomethicone | 6.00 | 6.00 |
| Preservative, fragrance | q.s. | q.s. |
| Triethanol amine | 0.1 | 0.1 |

Experimental Example 6

Measure of Effect for Increasing Skin Moisturizing Ability

The following experimental procedures are carried out to measure the effect of the theanine derivative to increase the skin moisturizing ability.

60 male or female adults with dry skin in their 40s or 50s are divided into two groups, 30 people each, and asked to apply the nutrient creams in the two test groups according to Example 2 and Comparative Example 2 on the face twice a day for 4 weeks. Skin hydration levels are measured using a Corneometer CM825 (Courage+Khazaka Electronic Co., Germany) under constant temperature and humidity conditions (24° C., relative humidity 40%). The measurements are taken prior to the start of application, one week, two weeks and four weeks after the start of application, and two weeks after interruption of application (i.e., six weeks after the start of application).

The increment of the skin hydration level at each time is calculated in percentage based on the skin hydration level prior to the start of application. The results are presented in Table 4.

TABLE 4

| Test group | Skin hydration level increment (%) | | | |
| --- | --- | --- | --- | --- |
| | After 1 week | After 2 weeks | After 4 weeks | After 6 weeks |
| Example 2 | 33 | 40 | 43 | 34 |
| Comparative Example 2 | 30 | 32 | 31 | 22 |

As can be seen from Table 4, Comparative Example 2 increases the skin hydration level by about 30% after 4 weeks of applications but decreases the skin hydration level after the interruption of its application. Contrarily, Example 2 containing the theanine derivative still increases the skin hydration level by about 30% or greater even after the interruption of its application. This demonstrates that the composition of the present invention containing the theanine derivative has a very excellent skin moisturizing effect.

Experimental Example 7

Examination of Effect to Improve Skin Wrinkle

The following experimental procedures are carried out to examine the effect of the composition of the present invention for improving the skin wrinkles.

80 healthy female adults in their 40s are divided into two groups, 40 people each, and asked to apply the nutrient creams according to Example 2 and Comparative Example 2 on the face once a day for 12 weeks. Replicas are prepared using silicone and subjected to image analysis with a visiometer (SV600, Courage+Khazaka electronic GmbH, Germany) to measure the state of skin wrinkles. The results of the image analysis are presented in Table 5. Each value in Table 5 is calculated an average of the values obtained by subtracting each parameter value before the application from each parameter value after 12 weeks of applications.

TABLE 5

| | Clinical result after 8 weeks of application | | | | |
| --- | --- | --- | --- | --- | --- |
| | R1 | R2 | R3 | R4 | R5 |
| Comparative Example 2 | 0.28 | 0.20 | 0.26 | 0.03 | 0.03 |
| Example 2 | −0.19 | −0.10 | −0.16 | −0.03 | −0.03 |

R1: difference between the highest value and the lowest value of the wrinkle contour line
R2: average of five R1 values of the wrinkle contour line randomly divided into 5 portions
R3: the highest value of the five R1 values
R4: average of the difference between the peak and the valley on the baseline of the wrinkle contour line
R5: difference between the baseline of the wrinkle contour line and the wrinkle contour As can be seen from Table 5, the skin preparation composition for external use according to the present invention has a very excellent effect to improve skin wrinkles. Therefore, the skin preparation composition for external use containing the theanine derivative according to the present invention is very effective in improving the skin wrinkles.

The present invention can provide a skin preparation composition for external use containing the theanine derivative as an active ingredient that benefits from the physiological activities of the theanine derivative to have excellent and differentiated physiological efficacies, more than imitating the effects of theanine mother nuclei, such as providing an anti-aging effect, improving skin wrinkles, strengthening skin barriers and skin immunity, and improving skin moisturization and atopic skin troubles.

What is claimed is:

1. A skin preparation composition for external use comprising a theanine derivative represented by the following formula 1 or 2 as an active ingredient:

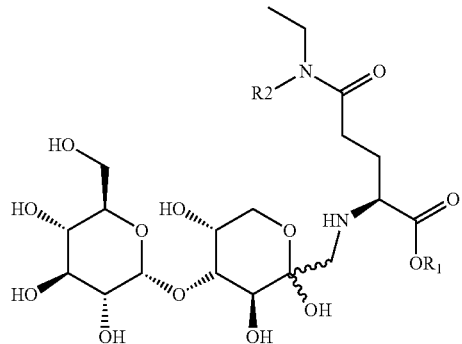

Formula 1 wherein $R_1$ is selected from the group consisting of hydrogen, methyl, ethyl, propyl, isopropyl, n-butyl, isobutyl, and tert-butyl; and $R_2$ is selected from the group consisting of hydrogen, methyl, ethyl, propyl, isopropyl, n-butyl, isobutyl, and tert-butyl,

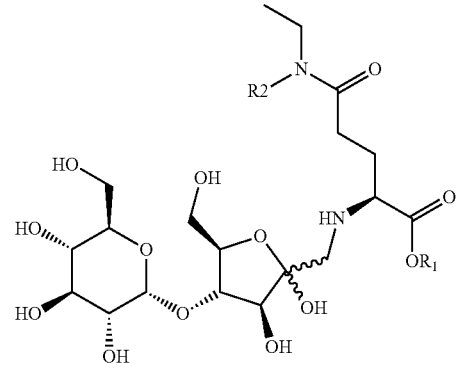

Formula 2 wherein $R_1$ is selected from the group consisting of hydrogen, methyl, ethyl, propyl, isopropyl, n-butyl, isobutyl, and tert-butyl; and $R_2$ is selected from the group consisting of hydrogen, methyl, ethyl, propyl, isopropyl, n-butyl, isobutyl, and tert-butyl.

2. The skin preparation composition for external use as claimed in claim 1, wherein the skin preparation composition comprises 0.0001 to 20 wt. % of the theanine derivative with respect to the total weight of the composition.

3. The skin preparation composition for external use as claimed in claim 1, wherein the composition promotes expression of Keratin 1 gene.

4. The skin preparation composition for external use as claimed in claim 1, wherein the composition promotes expression of transglutaminase 1.

5. The skin preparation composition for external use as claimed in claim 1, wherein the composition promotes expression of filaggrin.

6. The skin preparation composition for external use as claimed in claim 1, wherein the composition regulates migration of calcium in cells.

7. The skin preparation composition for external use as claimed in claim 1, wherein the composition is for anti-aging.

8. The skin preparation composition for external use as claimed in claim 1, wherein the composition is for improving skin wrinkles.

9. The skin preparation composition for external use as claimed in claim 1, wherein the composition is for improving skin homeostasis.

10. The skin preparation composition for external use as claimed in claim 1, wherein the composition is for strengthening skin barrier.

11. The skin preparation composition for external use as claimed in claim 1, wherein the composition is for strengthening skin immunity.

12. The skin preparation composition for external use as claimed in claim 1, wherein the composition is for skin moisturization.

13. The skin preparation composition for external use as claimed in claim 1, wherein the composition is for improving atopic disease.

14. A method for alleviating a symptom of atopic dermatitis comprising applying the skin external composition of claim 1.

15. A method for alleviating a symptom of atopic dermatitis comprising applying the skin external composition of claim 2.

* * * * *